(12) United States Patent
Mäki et al.

(10) Patent No.: US 7,361,480 B2
(45) Date of Patent: Apr. 22, 2008

(54) METHOD AND MEANS FOR DETECTING GLUTEN-INDUCED DISEASES

(76) Inventors: Markku Mäki, Ketunkatu 10, Tampere (FI) 33530; Ilma Korponay-Szabo, Alkotmány u. 20, H-1054, Budapest (HU)

(*) Notice: Subject to any disclaimer, the term of this patent is extended or adjusted under 35 U.S.C. 154(b) by 472 days.

(21) Appl. No.: 10/475,786

(22) PCT Filed: Apr. 24, 2002

(86) PCT No.: PCT/FI02/00340

§ 371 (c)(1), (2), (4) Date: Dec. 3, 2003

(87) PCT Pub. No.: WO02/086509

PCT Pub. Date: Oct. 31, 2002

(65) Prior Publication Data

US 2004/0115750 A1 Jun. 17, 2004

(30) Foreign Application Priority Data

Apr. 25, 2001 (FI) .................................. 20010868

(51) Int. Cl.
*G01N 33/537* (2006.01)
*G01N 33/564* (2006.01)
*G01N 33/573* (2006.01)

(52) U.S. Cl. ............... 435/7.4; 435/7.94; 435/7.95; 435/961; 436/506; 436/507; 436/513; 436/518; 436/538; 436/539; 436/540; 436/541

(58) Field of Classification Search ............... 435/7.4, 435/7.94, 7.95, 961; 436/506, 507, 513, 436/518, 538–541
See application file for complete search history.

(56) References Cited

U.S. PATENT DOCUMENTS

| | | | | |
|---|---|---|---|---|
| 5,139,932 A | * | 8/1992 | Cederholm et al. | 435/7.9 |
| 5,200,344 A | * | 4/1993 | Blaser et al. | 435/7.32 |
| 5,798,220 A | * | 8/1998 | Kossovsky | 435/13 |
| 6,319,726 B1 | * | 11/2001 | Schuppan et al. | 436/506 |
| 6,703,208 B1 | * | 3/2004 | Rajadhyaksha et al. | 435/7.2 |
| 2004/0115750 A1 | * | 6/2004 | Mki et al. | 435/7.92 |

FOREIGN PATENT DOCUMENTS

| WO | WO 9803872 A2 | 1/1988 |
|---|---|---|
| WO | WO 0101133 A2 | 1/2001 |

OTHER PUBLICATIONS

Harlow et al, Antibodies: A Laboratory Manual, Cold Spring Harbor Laboratory, 1988. pp. 175-181.*
Brenner et al., "Human Erythrocyte Transglutaminase Purification and Properties," Biochimica et Biophysica Acta, vol. 522, 1978, pp. 74-83.
Lorand et al., "Role of the intrinsic transglutaminase in the $Ca^{2+}$-mediated crosslinking of erythrocyte proteins," Proc. Natl. Acad. Sci. USA, vol. 73, No. 12, Dec. 1976, pp. 4479-4481.
Hansson et al., "Antibody Reactivity Against Human and Guinea Pig Tissue Transglutaminase in Children with Celiac Disease," Journal of Pediatric Gastroenterology and Nutrition, vol. 30, Apr. 2000, pp. 379-384.
Korponay-Szabo et al., J. Pediatr Gastroenterol Nutr., vol. 32, No. 3, pp. 361, Abstract 65, 2001.
Korponay-Szabo et al., J. Pediatr Gastroenterol, vol. 32, No. 3, pp. 361, Abstract 66, 2001.
Korponay-Szabo et al., J. Pediatr Gastroenterol Nutr., vol. 31, Suppl. 3, pp. S9, Abstract # 25, 2000.
Sardy et al., Clinical Chemistry, vol. 45, No. 12, pp. 2142-2149 (1999).
Sblattero et al. American Journal of Gastroenterology, vol. 75, No. 5, pp. 1253-1257 (Abs only) (2000).

* cited by examiner

*Primary Examiner*—David A. Saunders
(74) *Attorney, Agent, or Firm*—Birch, Stewart, Kolasch & Birch, LLP

(57) ABSTRACT

The invention is directed to a method of detecting gluten-induced diseases such as e.g. celiac disease and dermatitis herpetiformis. Said diseases are indicated by the presence of autoantibodies against tissue transglutaminase tTG in the blood The test is carried out on a whole blood sample using tTG liberated from the red blood cells of the blood sample as an autoantigen. The liberated autoantigens react with the autoantibodies in the sample and form antigen-antibody complexes, which are detected. The presence of such complexes indicates the disease. The invention is also directed to the use of the autoantigen in a test and to a test-kit.

13 Claims, 6 Drawing Sheets

METHOD AND MEANS FOR DETECTING GLUTEN-INDUCED DISEASES

This application is the national phase under 35 U.S.C. 371 of PCT International Application No. PCT/FI02/00340 which has an International filing date of Apr. 24, 2002, which designated the United States of America.

FIELD OF THE INVENTION

The present invention relates to the diagnosis, screening and following-up of diseases related to gluten intolerance such as celiac disease and other gluten-sensitive disease entities. More precisely the invention relates to a method of detecting gluten-induced diseases in a blood sample of a subject. The invention further relates to the use of an autoantigen in a detection method and to a test-kit useful in the method.

BACKGROUND OF THE INVENTION

Gluten-sensitive enteropathy is a genetically determined intolerance to dietary gluten, the harmful prolamins of wheat, rye and barley. The HLA alleles DQA1*0501 and DQB1*0201 encoding the HLA DQ2 heterodimer confer the genetic susceptibility to both celiac (also spelt coeliac) disease and dermatitis herpetiformis, the most commonly diagnosed disease forms belonging to this group. One or more so far unknown genes at HLA-unlinked loci most probably also predispose to celiac disease, where gluten ingestion leads to villous atrophy in the small bowel. The enteropathy is the result of gluten-triggered autoimmune processes and is self-perpetuating in the presence of gluten consumption. The immunological response is reduced and a mucosal healing is seen when gluten is excluded from the diet. The typical clinical manifestation of celiac disease is an overt malabsorption in young children or a severe wasting disease in adults. During the last decades it has become evident that celiac disease is underdiagnosed, the clinical features of the disease have changed to milder forms, and the diagnosis is often made at older age. Also in adult patients there is a shift towards milder symptoms. The true prevalence of celiac disease in different populations may be as high as one in 100.

The haplotype DR3-DQ2 is typical for many autoimmune disorders and is found in approximately 25% of the European population. Common celiac disease-associations are insulin-dependent diabetes mellitus, Sjögren's syndrome, autoimmune thyroiditis, rheumatoid arthritis, systemic lupus erythematosus and vitiligo. Further, the prevalence of autoimmune disorders in celiac disease is related to the duration of exposure to gluten. Untreated celiac disease patients also run an increased risk for malignancies and small-bowel lymphoma. Extraintestinal gluten-triggered manifestations are dermatitis herpetiformis, permanent-tooth enamel defects, osteopenia, liver involvement, cardiomyopathy, infertility, ataxia, and epilepsy with cerebral calcifications.

Small bowel biopsy is the cornerstone for celiac disease diagnosis. In addition to subtotal villous atrophy and crypt hyperplasia, a typical feature for the gluten-induced gut mucosal lesion is a high density of intraepithelial γδ+T lymphocytes. However, biopsy is an invasive diagnostic tool and is unsuitable for screening purposes. Certain serum autoantibodies, i.e. reticulin and endomysial antibodies, are gluten-induced, directed against the patient's own tissue extracellular matrix, and they are highly celiac disease-specific. Typically, these antibodies are found in IgA class, but celiac patients with selective IgA deficiency produce similar antibodies in IgG class (Collin P et al. Scand J Gastroenterol 1992;27:367-71). Recently, the enzyme tissue-type or cellular transglutaminase (tTG, EC 2.3.2.13, in the followings referred as transglutaminase) was identified as the target autoantigen of both endomysial and reticulin autoantibodies. Serological test based on the detection of these antibodies can be used to identify patients with mild or a typical symptoms and among subjects suffering of associated diseases, and even in the population. Case finding by screening has became the key in diagnosing gluten-enteropathy in recent years and some countries have started even mass screening of the school age population. There is an accumulating evidence, that the spectrum of gluten-sensitive diseases is broader than the classical gluten-enteropathy and may represent a general health care issue.

The reliable and reproducible perfomance of these antibody tests has only been achieved in specialized laboratories with the current methods. The reticulin and endomysial antibody assays require frozen tissue substrates, immunfluorescent equipments and a highly trained personnel to visually evaluate the antibody binding results. Importantly, the transglutaminase-based ELISA tests yield observer non dependent and quantitative results. However, their crucial component is the transglutaminase antigen which should preferably be as similar to the natural human autoantigen as possible. The $Ca^{2+}$-induced catalytically active conformation seems to be the preferred antigen recognized by the majority of patient autoantibodies, but the epitope specificity of individual patients may differ. It is difficult to maintain the correct folding of the enzyme during purification from animal tissues or to achieve it when producing recombinant transglutaminase proteins. In addition, transglutaminase is very sensitive to storage even at −40° C. and therefore the continuos need for appropriate and fresh antigen lots may make the transglutaminase antibody test very expensive. Commercially only tissue transglutaminase purified from guinea pig liver (Sigma) is available, but this rodent transglutaminase was found to be less sensitive in detecting celiac antibodies than the natural human enzyme prepared from human red blood cells (Hansson et al. J Pediatr Gastroenterol Nutr 2000;30:379-84).

There is a need for a simple serological screening test for celiac disease and related gluten-sensitive disease entities. Such a test would preferably be performed when the first suspicion for the celiac condition or other gluten-sensitive disease entities arises, thus in the primary case or as a mass-screening. It should also be applicable to following-up of already diagnosed patients. The present invention now provides a quick, cheap and accurate method of diagnosing gluten-induced diseases.

SUMMARY OF THE INVENTION

It has now surprisingly been found that intact human tissue transglutaminase tTG antigen is found in whole blood samples inside the red blood cells (RBC) in an amount sufficient to serve as antigen in an assay for autoantibodies against tTG. Thus there is no need to add external transglutaminase for the measurement of circulating transglutaminase autoantibodies. The antigen only has to be liberated from the RBCs by haemolysis which allows the transglutaminase and the specific transglutaminase antibodies to react in the liquid phase of the sample itself to form autoantigen-autoantibody complexes. Another advantage achieved by using autoantigens in the assay is that the test is insensitive to individual variations in the tTG antigens among different persons.

The method of detecting gluten-induced diseases according to the present invention is characterized in that a blood sample containing red blood cells (RBC) is hemolysed to liberate tissue transglutaminase (tTG) from the RBCs in the sample, the liberated tTG is allowed to react with possible anti-tTG autoantibodies in the sample to form an antigen-antibody complex, and said complex is assayed, whereby the presence of said complex indicates a gluten-induced disease. The method of the present invention may also be characterized in that a hemolysed blood sample of said subject is reacted with a tTG capturing protein after which any captured antigen-antibody complex is assayed, whereby the presence of said complex indicates a gluten-induced disease.

The invention further includes the use of tissue transglutaminase (tTG) liberated from the red blood cells (RBCs) of a blood sample in an assay for detecting anti-tTG autoantibodies in said sample, whereby the presence of said autoantibodies indicates a gluten-induced disease.

Still another object of the invention is a test-kit useful in the method disclosed. The test-kit is characterized in that it comprises means for assaying an antigen-antibody complex formed between liberated tissue transglutaminase (tTG) and anti-tTG autoantibodies in a blood sample.

Advantagous embodiments of the present invention are set forth in the dependent claims.

DETAILED DESCRIPTION OF THE INVENTION

Figure 1:
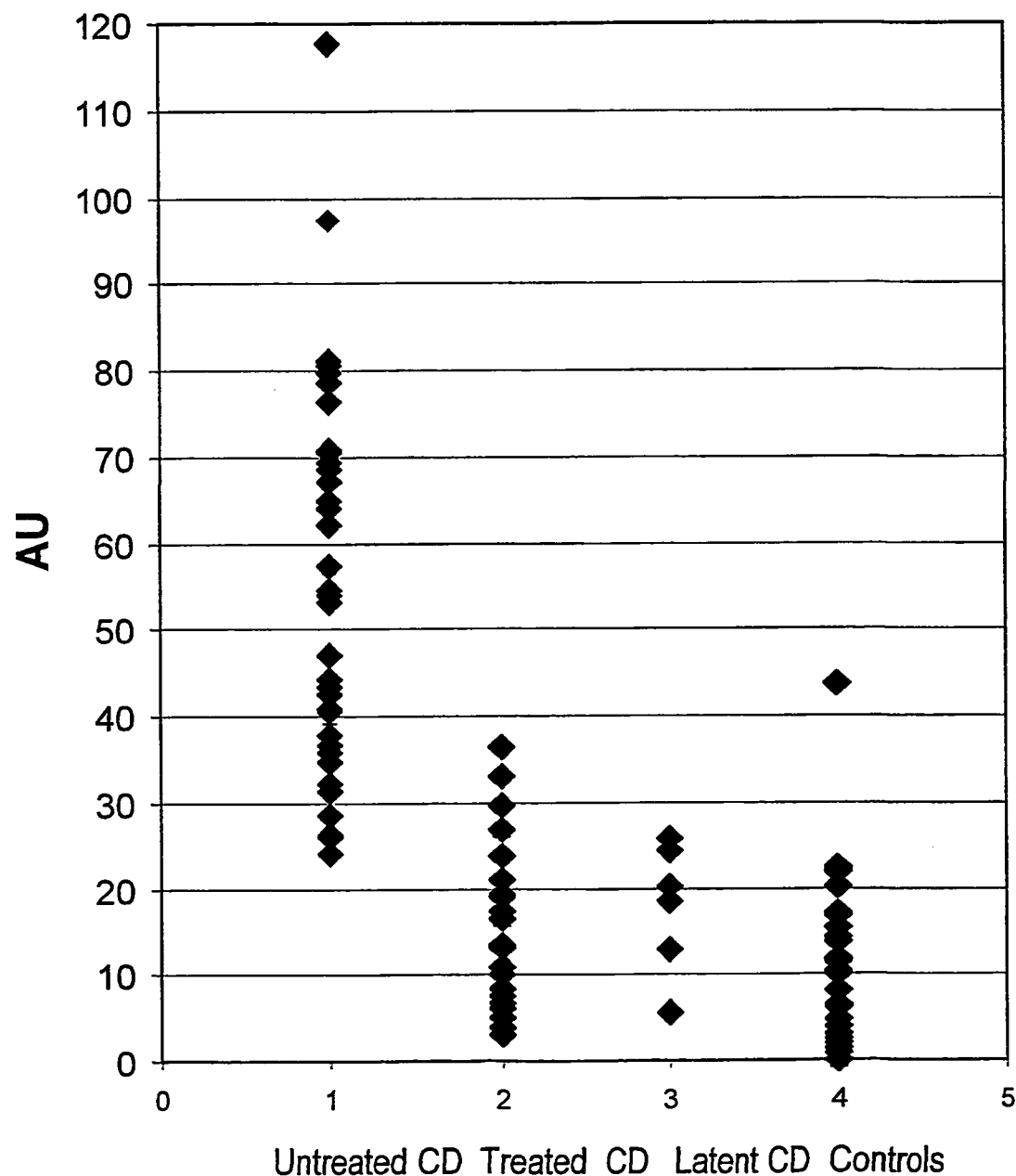
FIG. 1 shows transglutaminase-specific patient IgA measured by the whole blood test using haemolysed blood samples and IgG class anti-tTG capture antibodies immobilised on ELISA plate. The bound IgA was measured with peroxidase-conjugated anti-IgA. Results are given in arbitrary units (AU), as percentage of optical density measured with a positive reference sample and plotted for patients with untreated, treated or latent coeliac disease (CD) as well as for controls.

"Gluten-induced disease" as used herein relates to any gluten-induced disease entity or disorder, which is associated to autoantibodies against tissue transglutaminase tTG. Gluten-induced diseases often cause enteropathy and the most well known gluten-induced diseases are celiac disease and dermatitis herpetiformis. However, nowadays we know that there are also gluten-induced diseases without symptoms of enteropathy. Therefore a better indicator of a gluten-induced disease is the occurence of tTG autoantibodies.

The "tTG capturing protein" as mentioned here means any protein capable of binding the tTG-anti-tTG complex, or a compound associated to said complex, such as fibronectin. Preferably the tTG capturing protein is an antibody against tTG, or fibronectin, which is known to bind to tTG. It can even be a fibronectin antibody, which is capable of capturing the tTG-anti-tTG complex, because said complex also binds fibronectin present in the sample. Thus the fibronectin antibody binds the fibronectin of the fibronectin-tTG-anti-tTG complex formed. Said complex may also be captured by gelatin. Good results are obtained using human anti-tTG IgG obtained from IgA deficient patients as tTG capturing protein. Preferably a mixture of at least two such IgG antibodies with different epitope specificity are used.

The "means for assaying" the antigen-antibody complex includes any reagents necessary for indicating the complex formed. Said means may consist essentially of means for capturing the complex and means for detecting the captured complex. The means for detecting the complex are preferably reagents needed for an enzyme linked immunosorbent assay (ELISA). In one embodiment of the invention the capturing means comprise anti-tTG antibodies attached to a solid support and the detecting means comprise labelled anti-IgA and reagents necessary for the detection of the label.

A blood sample is taken from a subject suspected to be gluten-intolerant. The blood sample to be tested should contain red blood cells, which are hemolysed. The hemolysis can be carried out in any conventional way which disrupts the red blood cells so that tTG is liberated. Freezing and thawing is on possibility and the use of a hypotonic solution, e.g. water is another.

The invention provides an improved antibody binding assay for the diagnosis, differential diagnosis, screening and follow-up of genetical gluten intolerance, including celiac disease, dermatitis herpetiformis, gluten-sensitive subjects in associated diseases and the celiac trait characterised by the production of antibodies against transglutaminase. Intact human transglutaminase antigen is found in whole blood patient samples inside the red blood cells (RBC) and there is no need to add external transglutaminase for the measurement of circulating transglutaminase autoantibodies. The antigen only has to be liberated from the RBCs by haemolysis which allows the transglutaminase and the specific transglutaminase antibodies to react in the liquid phase of the sample itself. Then the antigen-antibody complexes are captured to a solid surface by suitable capture antibodies, proteins (e.g. fibronectin) or chemicals targeting the tissue transglutaminase antigen. After washing out the unbound components, the binding partners can be measured with immuno-chemical methods.

In another embodiment of the invention the patients' red blood cell transglutaminase content or one of other transglutaminase-associated compounds such as e.g. Fibronectin are measured based on the same principle.

The protein binding assay is preferably an immunoassay selected from radioimmunoassay (RIA), enzyme-linked immunosorbent assay (ELISA), fluoroimmunoassay (FiA), immunoradiometric assay (IRMA), immunoenzymometric assay (IEMA), immunoluminescence assay and immunofluorescence assay (Madersbacher S, Berger P. Antibodies and immunoassays. Methods 2000;21:41-50).

The method according to the present invention can be applied also to simple color detection systems (for example Nunc-Immuno Stick) which can work at the bedside or in doctor's offices. It requires only 10-50 microliters of whole blood, therefore it can be performed also from capillary blood by finger stick and it is not needed to obtain venous blood or serum.

EXAMPLE 1

Materials and Methods
Patients

Patient samples were collected at the Heim Pal Children's Hospital, Budapest, from patients attending jejunal biopsy for the suspicion of celiac disease (CD) or dermatitis herpetiformis (DH) as well from treated patients diagnosed earlier with these diseases. CD was diagnosed according to the current criteria of the European Society of Paediatric Gastroenterology, Hepatology, and Nutrition, comprising the demonstation of jejunal villous atrophy in histology and a clear clinical improvement on a gluten-free diet as well as the exclusion of other enteropathies. DH was diagnosed with skin biopsy direct immunoflurescent study by the presence of granular IgA deposits in the dermal papillae of the uninvolved skin adjacent to the visible skin lesions. In the first experiment samples from 84 gluten-sensitive patients (51 untreated, including 5 untreated DH; 6 latent, 27 on a gluten-free diet) with a median age of 4.7 years (range: 1-31), and from 10 non-celiac disease controls with normal jejunal villous structure were tested. For control purposes, random hospital samples submitted for blood gas testing were used (n=38) Age of the controls was 0.4-13 years.

Further experiments were conducted with samples of 15 additional CD patients, 15 DH and 42 controls.

Sample Handling

Whole blood samples were collected into heparinised capillary tubes (Clinitubes Radiometer A/S, Copenhagen, Denmark), mixed with a magnetic stick and sealed with caps on both sides. Then the samples were haemolysed by freezing and stored until testing at −20° C. or below. For initial testing both venous blood and capillary blood obtained by finger stick were filled into the capillary tubes. Control testings were performed with venous blood collected into tubes (Vacutainer, Becton Dickinson, Meylan, Fance) with EDTA or sodium citrate. They were also frozen either as they were collected or the plasma and the red blood cells were frozen separately after centrifugation for 5 minutes with 4000 rpm.

Celiac Antibody Capture and Testing by ELISA

At the time of testing, the frozen whole blood samples were thawed, mixed again, left at room temperature for 15 minutes and diluted with 0.05 M Tris-buffered 0.15 M saline with 10 mM EDTA and 0.1% Tween 20 pH 7.4 (TTBS). Experiments were conducted with other solutions for dilution, including distilled water, Tris-buffered saline with 2.5 or 5 mM $CaCl_2$ and solutions containing albumin or normal serum of the species (rabbit) in which the secondary antibodies were produced.

Microtiter plates (Nunc Immuno-Plate Maxisorp, Nunc A/S Roskilde, Denmark) were coated with a mixture of two IgG class celiac antibodies with different epitope specificity obtained from IgA deficient celiac patients with active disease and highly positive IgG class endomysial and transglutaminase antibodies. The respective dilutions of the celiac capture serum samples were 1:1000 and 1:2000 in 0.03 M bicarbonate buffer, pH 9.6, and they were coated to the plate for one hour at room temperature. Thereafter, the plates were washed three times in TTBS. Further blocking of the plates with bovine serum albumin was not used. The plates were incubated for one hour with the diluted whole blood samples at room temperature. After extensive washings in TTBS, the bound IgA class patient antibodies were measured with peroxidase-labelled rabbit antibodies against human IgA (DAKO A/S, Glostrup, Denmark) diluted 1:2000 in TTBS. The color was developed with 1 mg/ml o-phenylenediamine dihydrochloride (DAKO) with 0.06% $H_2O_2$ in 0.1 M Sodium citrate, pH 4.2 and was read spectrophotometrically at 450 nm.

In some experiments, the ELISA reaction was stopped with 2.5 M $H_2SO_4$ and the absorbance was measured at 492 nm as well. The samples were tested in two replicates. A known positive sample and blanks were included in each run. The antibody concentration was given both as optical densities and in arbitrary units calculated as the percentage of the positive reference sample.

In further experiments also other capture antibodies were tested, including polyclonal goat antibodies against tissue transglutaminase (Upstate Biotechnology, Lake Placid, N.Y.) and different monoclonal mouse antibodies against tissue transglutaminase (CUB7402 and TG100 from Neomarkers, Fremont, Calif.) as well as other IgG class patient antibodies. For the immobilisation of the monoclonal antibodies, a polyclonal rabbit antibody against mouse IgG1 (ICN Biomedicals Inc. Aurora, Ohio) diluted 1:500 in bicarbonate buffer was coated first to the plate and the monoclonals were added in TTBS.

Transglutaminase has a fibronectin-binding site at its N-terminal part and could even be purified from RBCs by the use of fibronectin (Radek et al. Proc Natl Acad Sci USA 1993;90:3152-6). Therefore, ELISA plates coated with human fibronectin (from Sigma F 2006, diluted 1:1000 in bicarbonate buffer, pH 9.6) also were tested for capture. As human plasma already contains some fibronectin, rabbit antibodies against human fibronectin (from DAKO, diluted 1:2000 in bicarbonate buffer, pH 9.6) were used as well as capture antibodies. The use of capture antibodies other than human IgG was introduced to make possible the testing of IgG class transglutaminase antibodies with the same principle by using secondary antibodies against human IgG instead of human IgA.

Testing for the Presence and Amount of Transglutaminase Captured to the ELISA Plates The amount of red blood cell transglutaminase bound to the plate was checked in separate wells coated with the capture antibodies and incubated with the haemolysed whole blood dilutions. The bound transglutaminase was measured with CUB7402, TG-100 monoclonal or polyclonal mouse antibodies against tissue trasnglutaminase followed by peroxidase-conjugated rabbit antibodies againt mouse immunoglobulins (DAKO). The color was developed similarly to the detection of bound IgA.

Testing for the Specificity of the Antigen/Antibody Capture

Control assays to the whole blood cell assay were performed with plasma or serum samples (diluted to similar final concentrations) from the same patients without or with adding normal red blood cell lysate diluted 1:20.

For further testing the specificity of the capture, a crude red blood cell lysate from blood donors' normal red blood cells diluted 1:20-1:40 was used as the antigen and the patient serum samples were added in a sandwich ELISA way, after washing out the unbound red blood cell lysate. The detection of the bound IgA was performed as in the whole blood ELISA. This sandwich-type serum ELISA was described in the abstract presented at the 8$^{th}$ International Symposium on Celiac Disease in Naples, 1999. The specificity of the sandwich ELISA system for transglutaminase measurements was further tested with 15 DH samples and 15 controls. As capture antibodies the celiac IgG, non-celiac IgG from an IgA deficient subject, monoclonal mouse anti-transglutaminase and irrelevant IgG1 class mouse monoclonal antibodies (DAKO) were used. The celiac patient IgG also was selectively coated to the plate by the use of monoclonal mouse antibodies against human IgG (Enzyme-Anti-IgG solution to Pharmacia Gluten IgA EIA kit, Pharmacia Diagnostics AB; Uppsala, Sweden). For the immobilisation of the monoclonal antibodies, a polyclonal rabbit antibody against mouse IgG1 (ICN) diluted 1:500 in bicarbonate buffer was coated first to the plate and the monoclonals were added in TTBS.

Serum Transglutaminase Antibody Testing with Rodent Antigen

Serum transglutaminase antibody detection by the use of rodent transglutaminase antigen (Sigma) was performed according to Sulkanen et al., Gastroenterology 1998; 115: 1322-1328.

EMA Testing

Serum endomysial antibodies were measured by an indirect immunofluorescent assay using 5-7 micrometer thick unfixed frozen sections of monkey oesoghagus (Korponay-Szabo et al. J Pediatr Gastroenterol Nutr 1997;25:56-63). The serum samples were initally tested at dilutions 1:2.5 and 1:10 in phosphate-buffered saline (PBS) and if positive, titrated further at dilutions 1:20, 40, 80, 160, 320, 640, 1280, 2560. The sections were incubated with the serum dilutions and after washings in PBS, the bound IgA patient antibodies were detected with fluorescein isothiocyanate-labelled rabbit antibodies specific for human IgA (DAKO). The positivity was assessed by a trained observer on the basis of the presence of IgA binding to the endomysial structures and subepidermal connective tissue fibers.

Results

Performance of the Whole Blood Celiac Test

The test was performing at whole blood patient sample dilutions 1:10-1:50. The dilution 1:25 was chosen for the further studies. The absorbance values for the plate-bound patient IgA were significantly higher for patients with untreated CD (optical density at 450 nm 0.417+0.245) than with the controls (0.094+0.045), p<0.001. Treated patients and patients in the latent phase of the disease had slightly elevated mean values, 0.145+0.060 and 0.141+0.043), respectively. These were not significantly different from the controls. Given that several runs were performed, for establishing the posivity cut-off level the results were expressed in arbitrary units (AU) calculated for the reference positive sample. The cut-off level, which detected all untreated CD patients was 23 AU. Only one control patient had AU values exceeding this cut-off. Thus the specificity of the test was 97.9% and clearly distinguished patients with active disease from the controls (FIG. 1). Mean AU for the untreated patients was 66.3 AU (95% confidence intervals, Cl: 55.1-77.4), and for the treated patients 15.6 AU (Cl:11.9-19.3), for the latent phase patients 17.9 AU (Cl:11.8-23.8). The mean of the controls was 7.2 AU (Cl:4.8-9.7).

Figure 2:
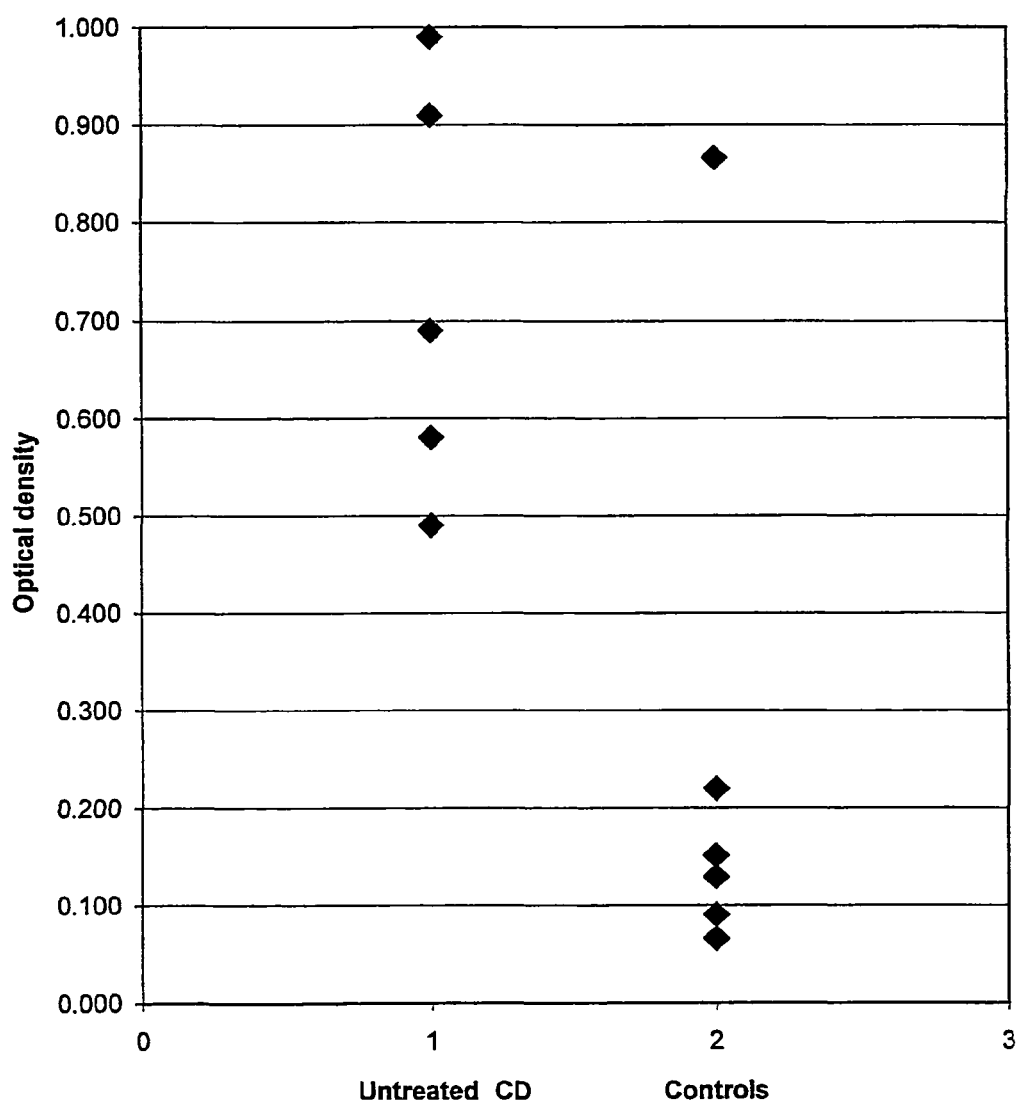
FIG. 2 shows results obtained with the whole blood samples of coeliac patients (CD) and controls using rabbit anti-fibronectin capture antibodies. The results are given as optical densities.

Pilot studies with 12 patient samples showed that also rabbit anti-fibronectin antibodies are able to efficiently capture the transglutaminase patient antibodies presumably via the transglutaminase antigen and the fibronectin in the sample (FIG. 2). One control subject (not biopsied) showed high O.D. and will be further investigated for possible CD. Fibronectin-coated plates also gave positivity, but the absorbance values were lower and less specific.

Testing for the Amount of Plate-Bound Transglutaminase

Figure 3:
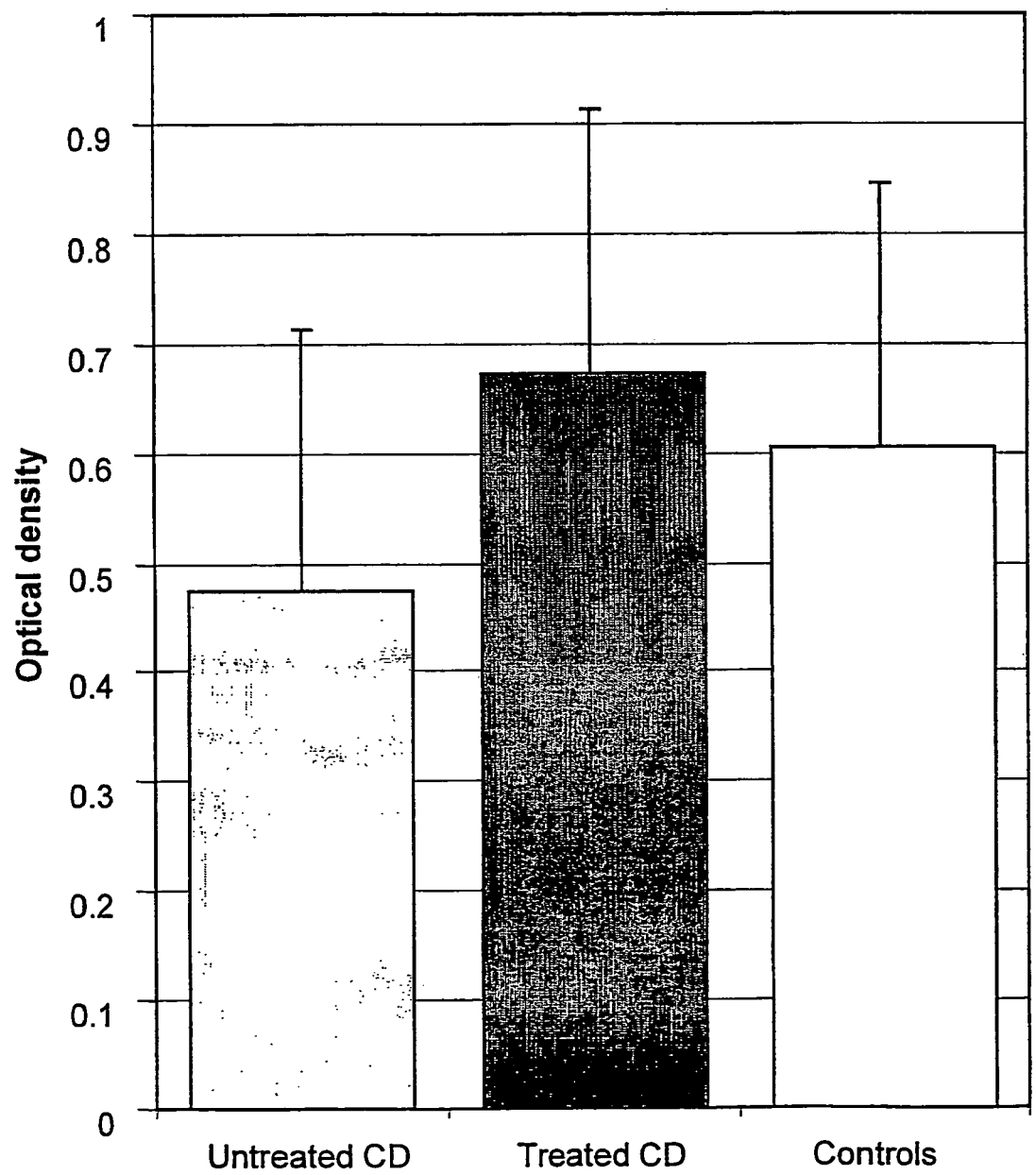
FIG. 3 shows the amounts of transglutaminase captured to the ELISA plate from the whole blood test samples by coeliac anti-tTG IgG antibodies. Transglutaminase was measured with monoclonal CUB 7402 antibodies. The results are given as optical densities.

The monoclonal antibody CUB 7402 detected comparable amounts of transglutaminase in the wells incubated with celiac or control samples (FIG. 3). P value was 0.16, not significant.

Testing for the Specificity of the Antigen and Antibody Capture

Figure 4:
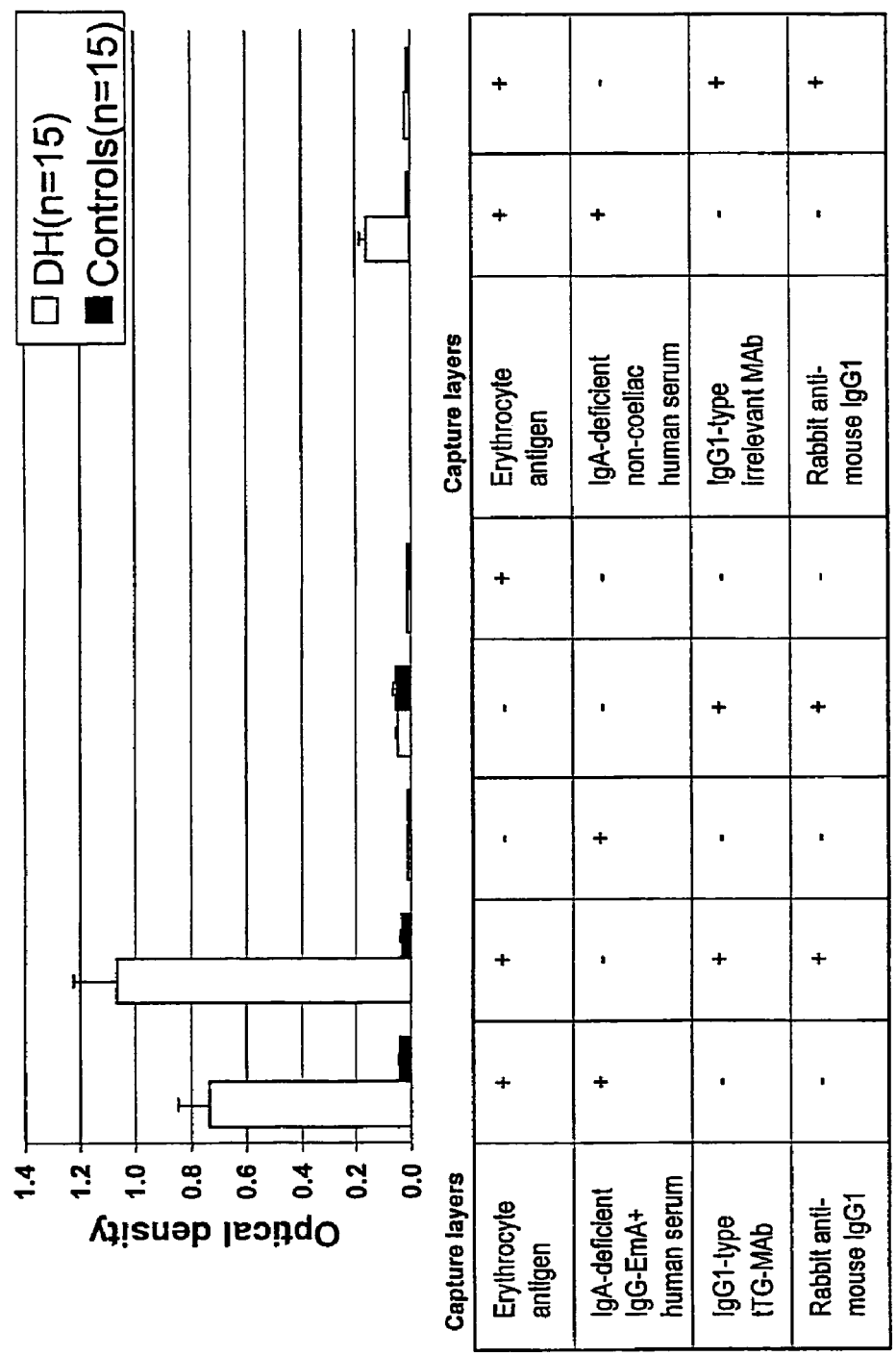
FIG. 4 shows testing of the capture system for the specificity for transglutaminase. Transglutaminase-specific and irrelevant capture antibodies (human IgG or monoclonal mouse IgG) were applied and a sandwich-type incubation with normal red blood cell transglutaminase antigen and patient serum samples (15 dermatitis herpetiformis patients and 15 controls) was done. The table indicates which components were included in the different capture settings and the superposed bars show the optical density values obtained in each setting.

Serum or plasma samples added to the capture antibodies without the red blood cells did not give specific positivity. When erythrocyte lysate was added to the plates coated with capture antibodies and the serum or plasma samples were only added after the unbound red blood cell components had been washed out (sandwich-type ELISA), a specific posivity was observed with the samples of gluten-enteropathy patients. The sandwich ELISA system was further explored with 15 dermatitis herpetiformis and 15 control samples. No specific absorbance values were seen, if either the erythrocyte-lysate or the transglutaminase-specific capture antibodies were omitted as well as substituted with irrelevant monoclonal antibodies or with a non-celiac IgA deficient human serum (FIG. 4). Selective coating of the IgG fraction from the IgA deficient celiac serum to the plate via monoclonal antibodies against human IgG resulted in similar positivity (optical density: 0.538±0.233) as the coating of the highly diluted whole celiac serum (0.735±0.304, not significant, p=0.07).

Comparison of the Whole Blood Test with Sandwich-Type Test Results

Figure 5:
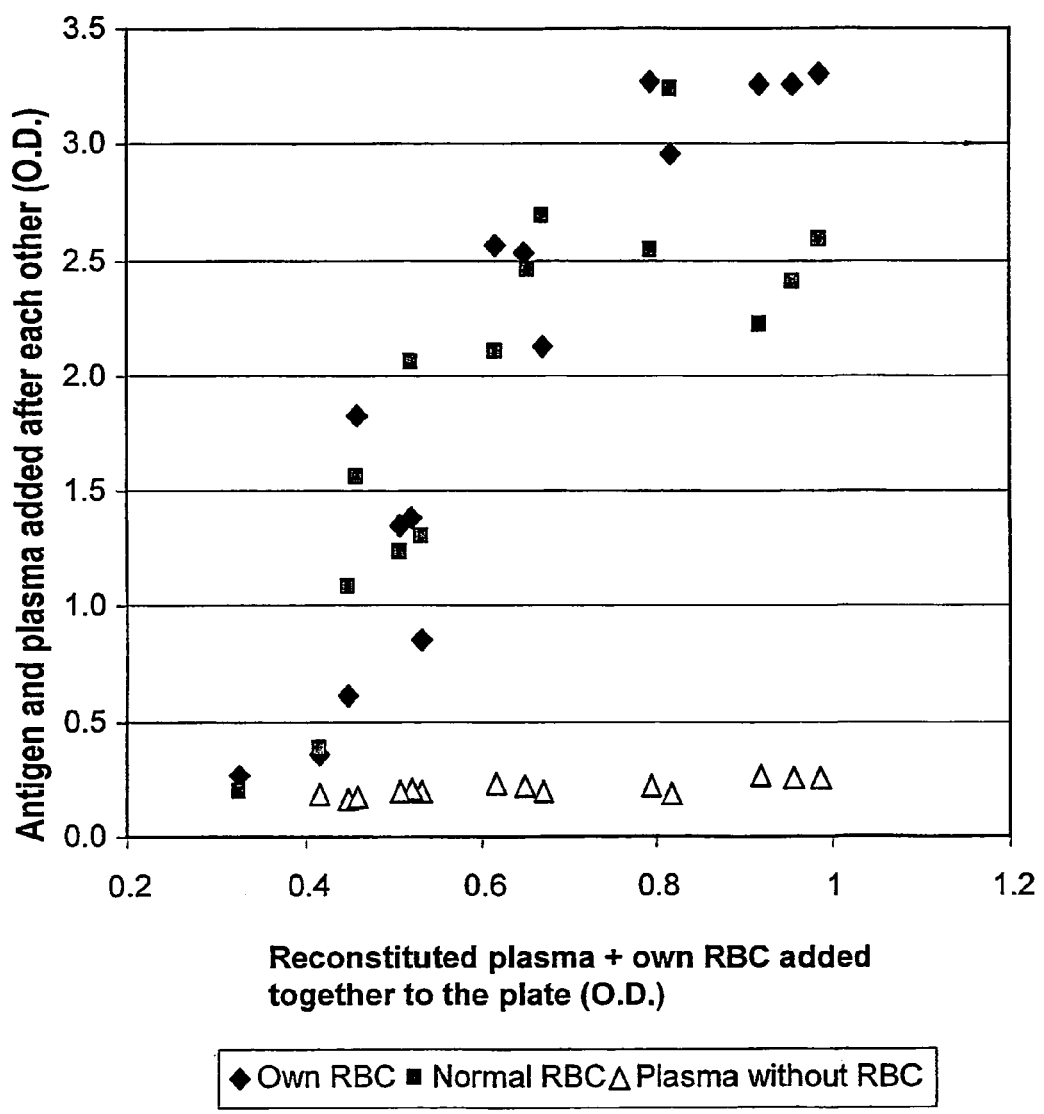
FIG. 5 shows the correlation of optical density values obtained with the use of whole blood samples (citrated plasma+citrated own RBC reconstituted) and the sandwich-type application of the red blood cell transglutaminase antigen followed by the incubation with patient plasma samples. In one setting, patients' plasma and red blood cell lysate were reconstitued and added together to the coeliac anti-tTG capture antibodies. In the other settings, normal red blood cell lysate or the patient's own red blood cell lysate was added to plates coated with the same type of capture antibodies. For control purposes, plasma samples were also added without red blood cells. Results are shown as optical densities.

In one setting, separately frozen citrated plasma and patient red blood cells (n=15) were reconstitued in similar ratio as the usual haematocrit (60:40) and added together to plates coated with the IgG celiac antibodies. In the other settings, first normal RBC or the patients' RBCs were added to the plate and plasma samples were inbubated after washing out the unbound RBCs (sandwich-type testing). The results in the two types of settings correlated well (FIG. 5).

Comparison of the Whole Blood Celiac Test Results with Conventional Antibody Test Results The whole blood test results for positivity strongly correlated with the results of both EMA and rodent transglutaminase test results obtained in the same untreated celiac patients and controls. One celiac patient had equivocal EMA and border-line rodent transglutaminase ELISA results. This patient was clearly positive in the whole blood test using her own antigen.

|  | Positive for serum EMA | Positive for serum antibodies reacting with rodent trans-glutaminase | Positive with the whole blood test |
|---|---|---|---|
| Untreated CD or DH | 50/51 | 51/51 | 51/51 |
| Treated CD | 0/27 | 3/27 | 5/27 |
| Latent CD | 5/6 | 4/6 | 2/6 |
| Controls | 0/26* | 1/26* | 1/48 |

*Only the controls with available serum samples were tested

EXAMPLE 2

Use of Alternative Capture Proteins

It was tested whether other proteins known to be able to bind to plasma fibronectin would also be suitable to capture endogenous fibronectin-transglutaminase-celiac patient autoantibody complexes found in the hemolysed patient samples.

Therefore, in additional experiments, ELISA plates were coated with either heparin (Noparin 5000 IU/ml, Novo Nordisk A/S, Denmark, diluted 1:500), laminin (Upstate, Lake Placid, N.Y., diluted 1:120, 12.5 ug/ml), collagen I (prepared from rat tail tendons according to Halttunen at al. Gastroenterology 1996;111:1252-1262, diluted 1:20, 80 ug/ml) or with 0.025-0.05% gelatin (Rousselot, Paris, France) dissolved in 0.03M bicarbonate buffer, pH 9.6. The further steps of the tests were carried out as in the whole blood test with human anti-transglutaminase IgG capture antibodies as described in Example 1.

Figure 6:
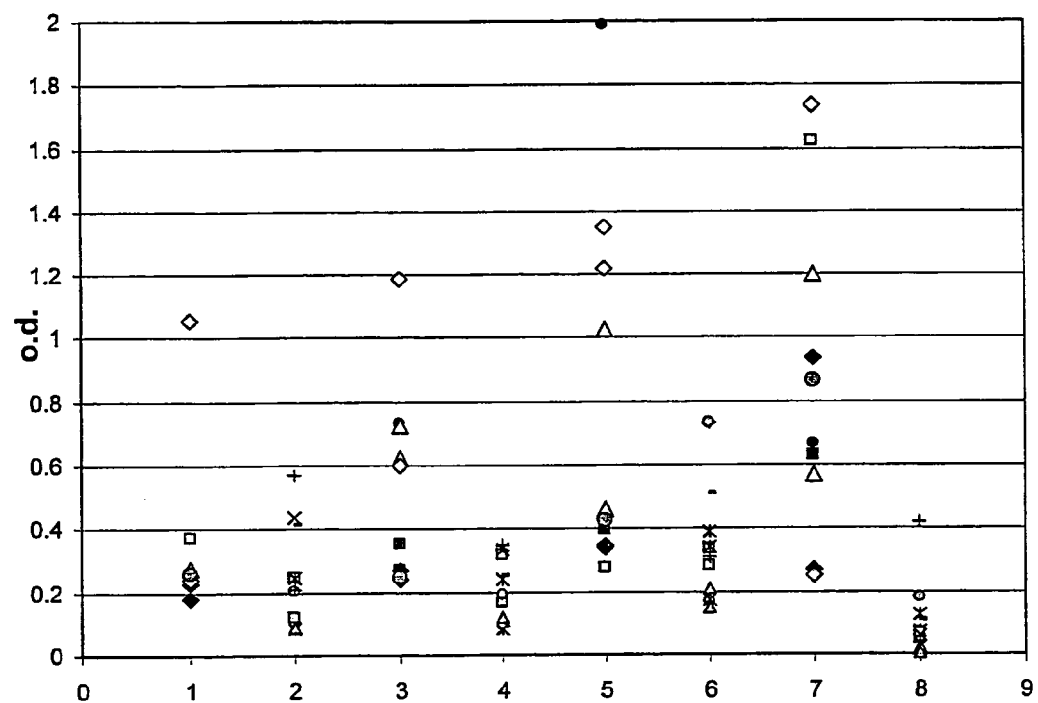
FIG. 6 shows capillary test results with heparin (1-2), laminin (3-4), collagen (5-6) and gelatin (7-8) as capture compounds, and the optical densities obtained with the haemolysed whole blood samples from celiac patients (n=10, columns 1, 3, 5, 7) and controls (n=12, columns 2, 4, 6, 8) when heparin (1-2), laminin (34), collagen I (5-6) or gelatin (7-8) were immobilised to the ELISA plates and used as capture compounds. The bound IgA was measured with peroxidase-conjugated anti-IgA. The same symbols represent the same samples in the different tests.

The results are set forth in FIG. 6. Heparin-coated plates did not give specific positivity with celiac patient samples. Laminin and collagen I seemed to capture the celiac antibody complexes, but the discrimination between the results with celiac samples and controls was not satisfactory. Gelatin was found to efficiently capture the celiac autoantibody-antigen complexes with high optical density and specificity. The optical densities were consistently higher than those observed with the whole blood test using human IgG capture antibodies from IgA deficient celiac patients. Probing the plates after the capture with the monoclonal tTG antibody CUB7402, it was found that higher amounts of transglutaminase were captured from the same whole blood samples to the plates by gelatin than by the human transglutaminase IgG antibodies (average optical density 1.485+/−0.727 versus 0.729+/−0.343). Therefore, a higher sample dilution could be applied that further increased the discrimination between celiac patient samples and controls.

In further testings with whole blood samples from 21 IgA-competent celiac patients and 62 controls using sample dilutions of 1:80, the optical densities for the celiac samples were 0.908±0.561 and those for the controls were 0.061±0.0480 when the plate-bound human IgA was measured at 492 nm. Treated celiacs (n=21) showed a mean value of 0.1981±0.248. At the cut-off where this test detected all untreated celiacs, 93.5% specificity was observed.

EXAMPLE 3

Detection of IgA Deficient Celiac Patients

The use of gelatin as a capture compound also enabled the measurement of captured antigen-autoantibody complexes from whole blood samples of IgA deficient celiac patients, because this capture protein did not interfere with the detection of transglutaminase-autoantibody complexes that might contain only IgG and but not IgA.

Therefore, the whole blood test with gelatin capture also was performed with an end-reaction that detects IgG class human antibodies bound to the plate using monoclonal antibodies against human IgG (from Pharmacia's Gluten EIA kit) and anti-mouse peroxidase-conjugated rabbit antibodies (DAKO). With this setting, the blood samples obtained from IgA deficient patients with active celiac disease (n=8) tested highly positive (mean optical density 0.824±0.284) while the mean optical density of the controls in the IgG detection was 0.118±0.053.

EXAMPLE 4

Correlation with Blood Hematocrit Values

In order to assess whether the performance of the whole blood test is influenced by the presence of anemia, which might decrease the amounts of the celiac autoantigen in the whole blood samples, the patients' respective hematocrit values were measured at the time of blood sampling in other clinical tests. The optical densities obtained with the whole blood test did not show correlation with the hematocrit values, neither in the celiac patients (R=0.076) nor in the whole material (R=0.068). Even at hematocrit values as low as 0.277 (severe anemia) positive results were obtained with the samples from celiac patients.

The invention claimed is:

1. Method of detecting gluten-induced diseases in a blood sample of a subject,
   said method comprising hemolysing a blood sample containing red blood cells (RBC) to liberate tissue transglutaminase (tTG) from the RBCs in the sample, allowing the liberated tTG to react with possible anti-tTG autoantibodies in the sample to form an antigen-antibody complex,
   and assaying said complex, whereby the presence of said complex indicates a gluten-induced disease.

2. The method of claim 1, wherein the disease to be detected is celiac disease (CD) or dermatitis herpetiformis (DH).

3. The method of claim 1, wherein the antigen-antibody complex is captured to a solid support by an antibody against tTG, fibronectin, an antibody against fibronectin, or gelatin and the captured complex is detected by an immunoassay.

4. The method of claim 3, wherein the tTG capturing protein is an anti-tTG antibody.

5. The method of claim 3, wherein the antigen-antibody complex is captured by human anti-TTG IgG.

6. The method of claim 3, wherein the IgG is a mixture of at least two human IgG antibodies with different epitope specificity and obtained from IgA deficient celiac patients.

7. The method of claim 3, wherein the antigen-antibody complex is captured by fibronectin or fibronectin antibody.

8. Presented) The method of claim 3, wherein the immunoassay is an enzyme linked immunosorbent assay (ELISA).

9. The method of claim 1, wherein
   i) a whole blood sample is hemolysed by freezing and thawing,
   ii) the sample is allowed to stand for a lime sufficient for the antigen-antibody complexes to be formed,
   iii) the sample is contacted with anti-TTG IgG on a solid support, and iv) the antigen-antibody complexes captured by the anti-TTG IgG on the solid support are detected by ELISA using anti-antibodies against human IgA.

10. Test-kit for use in the method of claim 1, said test-kit comprising:
(i) a tissue transglutaminase (tTG) capturing protein for capturing a tTG-anti-tTG antibody complex formed between liberated tTG and anti-tTG autoantibodies in a blood sample, said capturing protein being anti-tTG-antibodies; and
(ii) labelled anti-IgA or anti-IgG antibodies for detecting the captured tTG-anti-tTG antibody complex.

11. Test-kit of claim 10, wherein the capturing anti-tTG antibodies are attached to a solid support.

12. Test-kit of claim 10 or 11 further comprising reagents necessary for the detection of the label.

13. Method of detecting gluten-induced diseases in a hemolysed blood sample of a subject, said method comprising allowing tissue transglutaminase (tTG) liberated from the red blood cells during hemolysis of the sample to react with possible anti-tTG autoantibodies in the sample to form an antigen-antibody complex; and assaying said complex, whereby the presence of said complex indicates a guten-induced disease.

* * * * *